(12) United States Patent
Bedingfield et al.

(10) Patent No.: US 8,349,174 B2
(45) Date of Patent: Jan. 8, 2013

(54) PORTABLE POWER DIALYSIS MACHINE

(75) Inventors: John A. Bedingfield, Largo, FL (US); Richard E. Kienman, Tampa, FL (US); Brian C. Lauman, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1043 days.

(21) Appl. No.: 12/178,437

(22) Filed: Jul. 23, 2008

(65) Prior Publication Data
US 2010/0022937 A1 Jan. 28, 2010

(51) Int. Cl.
*B01D 61/30* (2006.01)
*B01D 61/28* (2006.01)
*B01D 61/24* (2006.01)

(52) U.S. Cl. ........ 210/143; 210/134; 210/175; 210/184; 210/252; 210/257.1; 210/258; 210/321.6; 210/416.1; 604/4.01; 604/6.09; 604/6.11; 604/6.13; 604/6.15; 604/6.16; 604/7; 604/27; 604/29

(58) Field of Classification Search .................. 210/175, 210/184, 185, 186, 194, 252, 256, 257.1, 210/258, 321.6, 416.1; 604/4.01, 5.01, 6.09, 604/6.11, 6.13, 6.15, 6.16, 7, 27, 29
See application file for complete search history.

(56) References Cited

U.S. PATENT DOCUMENTS

| | | | |
|---|---|---|---|
| 3,710,454 A * | 1/1973 | Mellor | 434/268 |
| 3,774,243 A | 11/1973 | Ng et al. | |
| 3,799,873 A * | 3/1974 | Brown | 210/641 |
| 3,837,922 A | 9/1974 | Ng et al. | |
| 3,878,564 A | 4/1975 | Yao et al. | |
| 3,919,722 A | 11/1975 | Harmison | |
| 3,941,135 A | 3/1976 | von Sturm et al. | |
| 3,963,567 A | 6/1976 | Cole | |
| 3,994,799 A | 11/1976 | Yao et al. | |
| 4,068,651 A | 1/1978 | Rappaport | |

(Continued)

FOREIGN PATENT DOCUMENTS

EP 0 005 266 11/1979

(Continued)

OTHER PUBLICATIONS

International Preliminary Report on Patentability for International Application No. PCT/US2009/051268 dated Nov. 16, 2010.

(Continued)

*Primary Examiner* — John Kim
(74) *Attorney, Agent, or Firm* — K&L Gates LLP

(57) ABSTRACT

A fuel-cell powered medical fluid processing machine or dialysis machine is disclosed. The machine is intended for remote or rural areas where standard household or utility power is not available or is subject to interruption. The fuel cell is powered by hydrogen or other source of protons, or may instead be powered by methanol or ethanol, such as a direct methanol fuel cell. The fuel cell may be operated directly, as in powering a portable, wearable dialysis device, or may be operated indirectly, to generate and store power in an electric power storage device of the medical fluid or dialysis device. The medical fluid processing machine or dialysis machine may include circuitry allowing for use by household or utility power while also including a fuel cell for use when other power is not available. A catalytic heater may be used to warm the dialysis fluid.

11 Claims, 8 Drawing Sheets

U.S. PATENT DOCUMENTS

| | | | |
|---|---|---|---|
| 4,247,393 A * | 1/1981 | Wallace | 210/638 |
| 4,659,634 A | 4/1987 | Struthers | |
| 4,765,907 A * | 8/1988 | Scott | 210/648 |
| 4,895,150 A | 1/1990 | Isaacson et al. | |
| 5,037,293 A | 8/1991 | Kirby | |
| 5,326,252 A | 7/1994 | Tonon | |
| 5,714,874 A | 2/1998 | Bonnefoy | |
| 5,842,851 A | 12/1998 | Pivot | |
| 6,248,469 B1 * | 6/2001 | Formato et al. | 429/494 |
| 6,342,071 B1 | 1/2002 | Pless | |
| 6,348,777 B1 | 2/2002 | Brown et al. | |
| 6,602,627 B2 | 8/2003 | Liu et al. | |
| 6,641,612 B2 | 11/2003 | Pless | |
| 7,153,285 B2 | 12/2006 | Lauman et al. | |
| 7,276,042 B2 | 10/2007 | Polaschegg et al. | |
| 7,374,833 B2 | 5/2008 | Stute | |
| 7,775,374 B1 * | 8/2010 | Barker et al. | 210/416.3 |
| 7,867,592 B2 * | 1/2011 | Nelson et al. | 428/40.1 |
| 8,034,235 B2 * | 10/2011 | Rohde et al. | 210/134 |
| 2002/0169416 A1 | 11/2002 | Gonnelli et al. | |
| 2005/0101901 A1 * | 5/2005 | Gura | 604/5.02 |
| 2005/0148913 A1 | 7/2005 | Weston | |
| 2007/0020142 A1 | 1/2007 | Federspiel et al. | |
| 2007/0213665 A1 | 9/2007 | Curtin et al. | |
| 2008/0006470 A1 | 1/2008 | Gura et al. | |
| 2008/0008609 A1 | 1/2008 | Pate et al. | |
| 2008/0015494 A1 | 1/2008 | Santini, Jr. et al. | |
| 2008/0044721 A1 | 2/2008 | Heller et al. | |
| 2008/0055826 A1 | 3/2008 | Smith et al. | |
| 2008/0086176 A1 | 4/2008 | Ofek | |
| 2008/0087170 A1 | 4/2008 | Deane et al. | |
| 2008/0217245 A1 * | 9/2008 | Rambod et al. | 210/637 |
| 2009/0120864 A1 * | 5/2009 | Fulkerson et al. | 210/198.1 |
| 2010/0022937 A1 * | 1/2010 | Bedingfield et al. | 604/6.09 |

FOREIGN PATENT DOCUMENTS

| | | |
|---|---|---|
| EP | 1 121 948 | 8/2001 |
| WO | WO 97/47335 | 12/1997 |
| WO | WO 2005/105179 | 11/2005 |
| WO | WO 2008/049029 | 4/2008 |

OTHER PUBLICATIONS

International Search Report and Written Opinion for International Application No. PCT/US2009/051268 dated Mar. 3, 2010.

* cited by examiner

PORTABLE POWER DIALYSIS MACHINE

BACKGROUND

This patent relates generally to power sources for medical fluid delivery systems. More particularly, this patent discloses systems, methods and apparatuses for fuel cell powered medical fluid delivery systems, such as dialysis machines.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is lifesaving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD").

CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient performs a drain, then a fill, and then allows the peritoneal dialysis fluid to dwell for a few hours. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems either clean or regenerate spent dialysate instead of discarding it, or they consume very large quantities of dialysate. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Each of the kidney failure treatment systems discussed above requires electricity, which is used to heat dialysis fluid for infusion into a patient's peritoneum in peritoneal dialysis. In hemodialysis, electricity is used to warm the dialysis fluid sent to the dialyzer, and may also be used to warm the patient's blood before it is returned to the patient. Electricity is used to power the peristaltic pumps or diaphragm pumps used to pump dialysis fluid or blood in these systems, and electricity is also used for the control systems, speakers, video outputs of dialysis machines.

Problems exist with prior dialysis systems, as described above, because as noted, the heating, pumping, metering and controlling steps are all accomplished using electricity. Thus, if a person requires dialysis treatment, the dialysis machine must be used in a location where electricity is available. Thus, dialysis may not be available to persons in remote or rural areas where electricity is not available. A need therefore exists for a power source that will provide electricity for dialysis machines, or more generally, for medical fluid delivery machines, where electricity is not available. It would also be advantageous if the power source were something other than a standard gasoline-fueled generator, because such generators are bulky and unwieldy. What is needed is a portable, low volume, low weight power source for medical fluid delivery machines, especially dialysis machines.

SUMMARY

Embodiments described herein overcome these problems by using fuel cells. A small fuel cell, such as a fuel cell using methanol or ethanol, is portable and provides electric power. One embodiment is a method for operating a medical fluid machine. The method includes steps of providing a portable fuel cell power source, connecting an output of the power source to a medical fluid machine, and operating the medical fluid machine, wherein the power source is powered by a liquid fuel and is at least as small, compact and portable as the medical fluid machine.

Another embodiment is a method for operating a dialysis machine. The method includes steps of providing a fuel cell source of electric power, connecting an electrical output of the fuel cell source to a dialysis machine, and operating the dialysis machine, wherein the fuel cell source is powered by a liquid fuel and is at least as small, compact and portable as the dialysis machine.

Another embodiment is a portable dialysis machine. The portable, wearable dialysis machine for a patient includes a fuel cell for powering the wearable dialysis machine, a pump powered by the fuel cell for pumping dialysis fluid in a fluid circuit, a particulate filter placed in the fluid circuit, and a replaceable cartridge in the fluid circuit for absorbing waste products.

Another embodiment is a dialysis machine. The dialysis machine includes a fuel cell for powering the dialysis machine, an electric power storage device connected to the fuel cell, a fluid circuit for dialysis fluid for the dialysis machine, the fluid circuit including an input line for fresh dialysis fluid, a fluid connection to a patient, and a drain for voiding spent dialysis fluid. The dialysis machine also includes at least one positive displacement pump powered by the fuel cell for pumping the dialysis fluid to and from the patient, at least one input device for controlling the dialysis machine, at least one output device for monitoring the dialysis machine, and a controller for controlling the dialysis machine, the controller operably connected to the at least one input device and output device.

Additional features and advantages are described herein, and will be apparent from the following Detailed Description and the figures.

DETAILED DESCRIPTION

The fuel cells described herein may provide primary or backup power for a medical fluid processing machine, such as a peritoneal dialysis machine or a hemodialysis machine. A fuel cell is a device which converts a fuel directly into electrical energy without burning the fuel to first produce heat and mechanical energy, and then converting the mechanical energy, such as a spinning turbine, into electrical energy. One example is a hydrogen fuel cell, such as a phosphoric acid fuel cell (PAFC), which operates at high temperatures. A phosphoric acid fuel cell uses a proton exchange membrane (PEM) to pass hydrogen ions (protons) through the membrane, where they are reacted with oxygen molecules to eventually form water, which is carried away from the membrane and disposed. Phosphoric acid fuel cells may be purchased from United Technologies Corp., East Hartford, Conn., U.S.A., and others. It may be powered by natural gas or methane produced from anaerobic digester gas (ADG). A PAFC typically reforms the methane fuel into hydrogen by reacting methane with water at high temperature to form hydrogen gas and carbon monoxide. The carbon monoxide is then shifted to carbon dioxide by a second reaction with water to form the carbon dioxide and additional hydrogen for immediate use in the fuel cell. Of course, hydrogen fuel cells may also be powered by hydrogen gas.

Fuel cells may instead be powered by liquid fuels, such as methanol or ethanol. Direct methanol fuel cells (DMFC) are available from a number of companies, such as Toshiba Corp., Tokyo, Japan, and MTI Micro, Albany, N.Y., U.S.A. Liquid-fueled fuel cells are more portable and easier to handle than fuel cells using PEM technology. A great variety of other fuel cells are commercially available from a number of manufacturers. These companies and others also sell replacement fuel cartridges These fuel cells can be advantageously used to power medical fluid therapy machines, such as dialysis machines, especially when the patient is located in an area where electric power is easily or often disrupted. It is important for the health and comfort of patients that the patient receives therapy on time. It is also important that once therapy has begun, it is completed. Thus, a dialysis machine that is in a remote or rural area may be powered primarily or secondarily by a fuel cell. In a methanol fuel cell, methanol is oxidized with water at the anode to form carbon dioxide, hydrogen ions, and electrons. At the cathode, oxygen is reduced by reaction with the hydrogen ions to produce water. Thus, water is present on both sides of the reaction, which tends to limit the energy density of the fuel cell. Such cells, however, are much easier to handle and operate at far lower temperatures.

Figure 1:
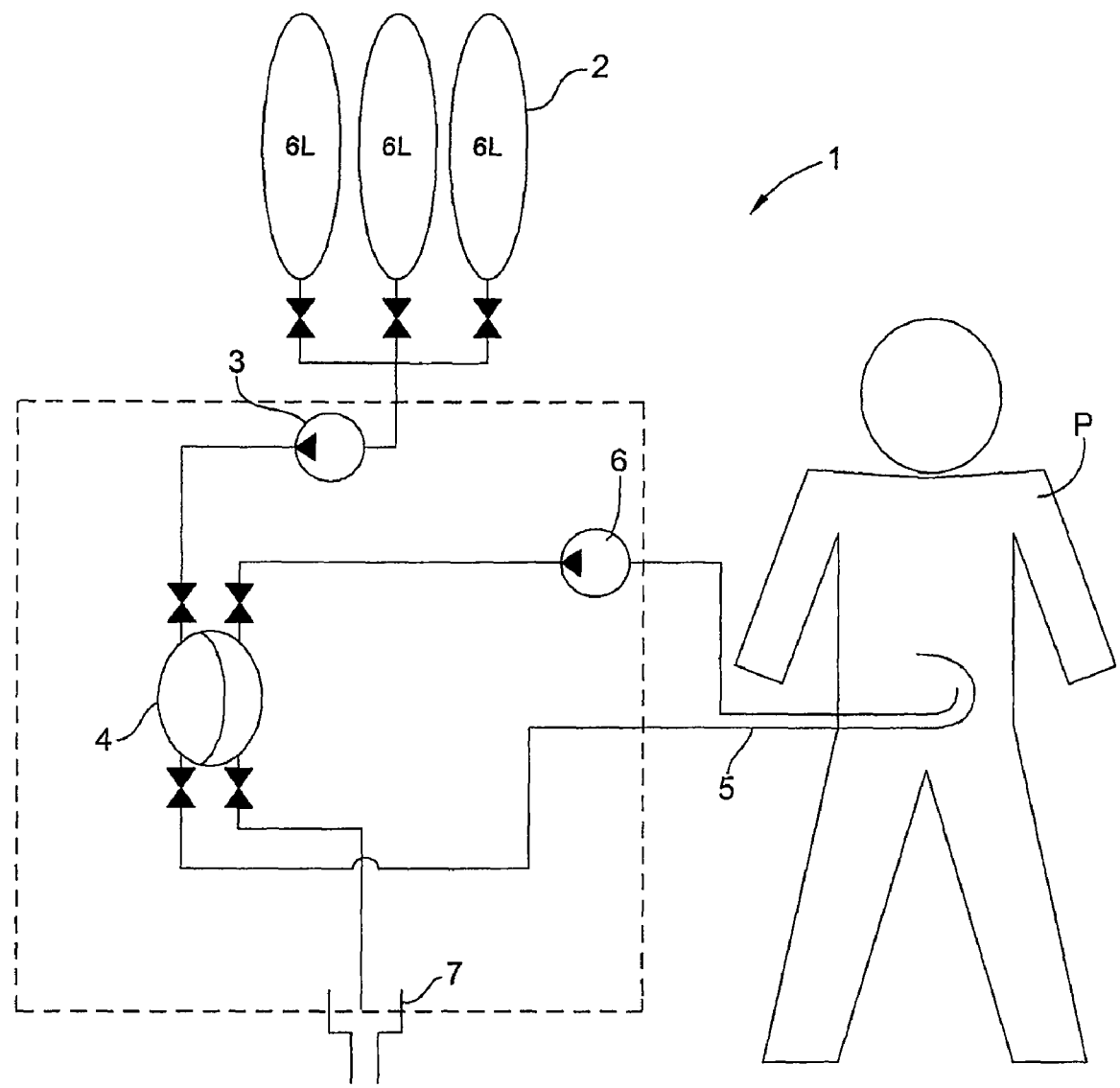
FIG. 1 depicts a prior art dialysis machine.

Dialysis therapy is typically conducted with a peritoneal dialysis machine, such as the machine depicted in FIG. 1. One suitable peritoneal dialysis machine is the HomeChoice® peritoneal dialysis machine from Baxter International, Deerfield, Ill., U.S.A. A patient P is connected to a dialysis fluid delivery system 1, shown within the dashed lines, with a patient access device 5, such as an implanted catheter as shown. The catheter may be a single lumen or double lumen catheter, or another type of access device may be used. A plurality of containers 2 of dialysis solution is connected to the dialysis machine, as shown, through valves or other connectors. A pump 3 is used to transport dialysis fluid from the containers 2, one at a time, through a balance chamber 4 to the peritoneal cavity of the patient P through the access device. After the peritoneal dialysis solution has remained within the patient for the desired dwell time, the same pump 3 or another pump 6 may be used to pump the spent dialysis solution through the balance chamber 4 and then to a drain 7.

Figure 2:
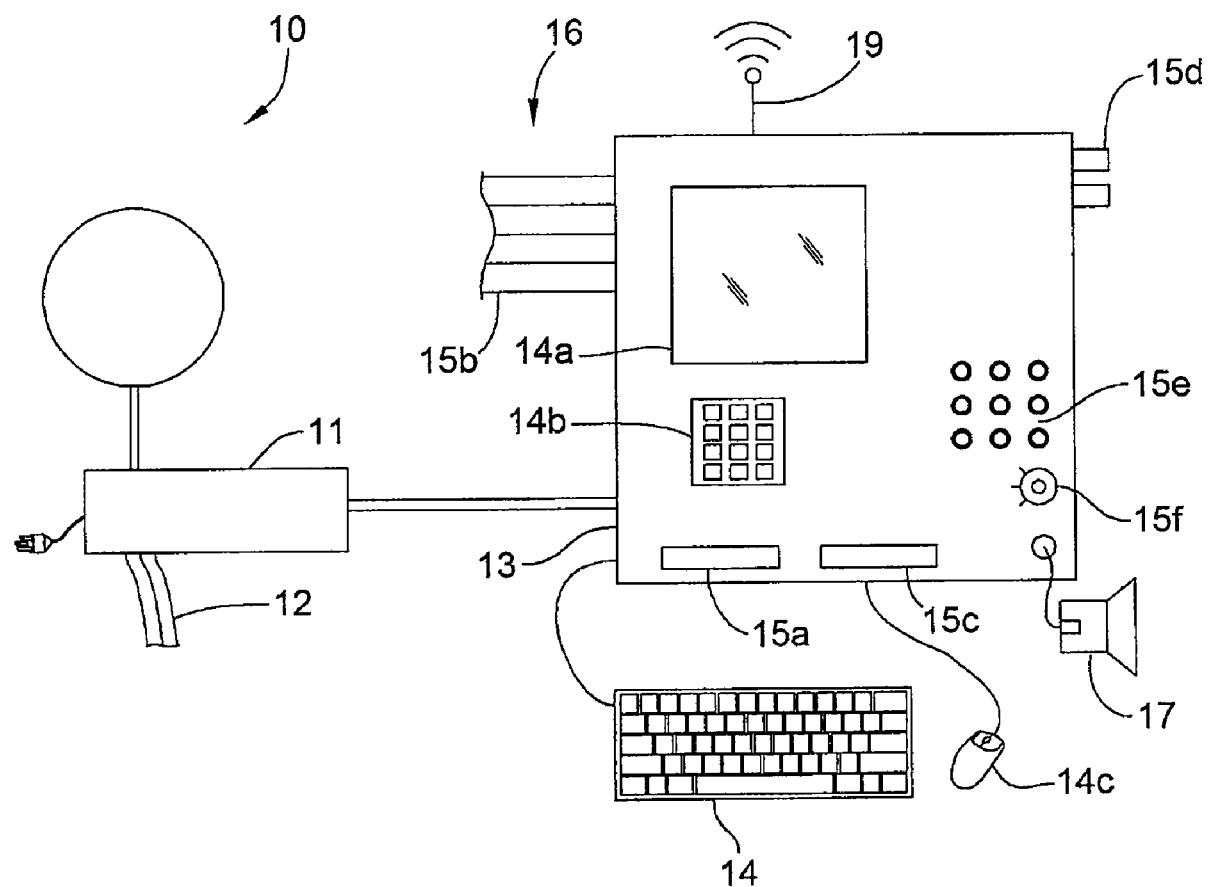
FIG. 2 depicts a control system for a fuel-cell powered dialysis machine.

In embodiments discussed herein, a dialysis fluid delivery system 1 is used with a dialysis control system, such as a control system 10, as depicted in FIG. 2. Dialysis control system 10 includes a dialysis fluid delivery system 11, such as the peritoneal dialysis delivery system depicted in FIG. 1, including fluid lines 12 for connection to patient access device 15. The dialysis fluid delivery system 11 performs dialysis for the patient under the supervision of a control unit 13. Control unit 13 in one embodiment has at least an input keypad 14, control panel 14a, which may be a touch screen, input number pad 14b, and mouse 14c. The control unit will also include input drive 15a, which may be suitable for a floppy drive or for a CD drive. The computer in this embodiment is configured with a port for Internet access 15b, as well as additional inputs and outputs, including ports 16. The additional input ports may be any combination of serial ports, such as USB ports, or parallel ports.

In some embodiments, the control unit will be adapted to receive commands from a remote control unit, and will include an IR receiver 15c for a hand-held remote. Inputs/outputs may include an optical input or output 15d and other digital or analog inputs. Control portion 15e includes a series of controls knobs or switches for operating the dialysis machine. A speaker output 17 can alert the patient or a caregiver if there is an emergency or other malfunction of the dialysis machine. There is also a visual alarm 15f for alerting the patient or caregiver. The control section includes an antenna 19 for receiving remote commands or information. The antenna may be used for communication with a wireless device for the patient, as discussed below. The antenna may also be used for wireless (WiFi) internet access or may be used for remote, but closer, commands.

Figure 3:
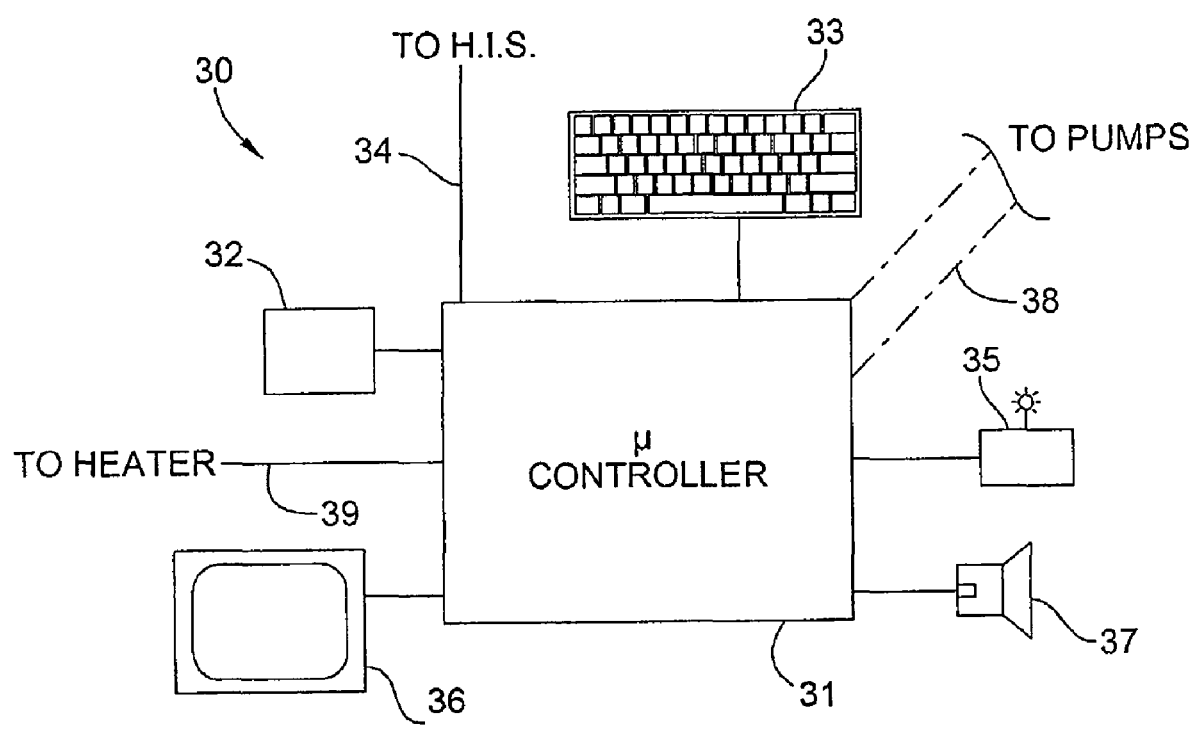
FIG. 3 depicts a fuel-cell powered dialysis machine.

FIG. 3 depicts a closer view of the control portions 30 of the dialysis machine 10. As seen in FIG. 3, the communication in this embodiment is wireless, for convenience and mobility of patients, such as mobile CAPD patients. However, those with skill in the art will recognize that a wire harness or cable could also connect the two portions. Dialysis machine control portion 30 includes a supervisory microcontroller 31, which receives power from a power source 32, such as a fuel cell, as either a primary or secondary power source. The dialysis machine may receive its primary power as household or utility power. The microcontroller receives inputs from at least a keypad 33, and may also receive data and commands from a wired connection 34, such as from a clinic or hospital information system. Inputs may also be received from the patient via wireless connection and radio 35. The microcontroller has outputs to a video monitor 36, a speaker 37, as well as controls to the dialysate pumps 38 and a heater 39 for the dialysate. The machine control system includes at least one memory as a part of the microcontroller 31 or accessible by the microcontroller 31. Not specifically shown in the diagram is circuitry for sensing a power interruption from a primary source, such as household power, and switching from household power to the fuel cell.

Figure 4:
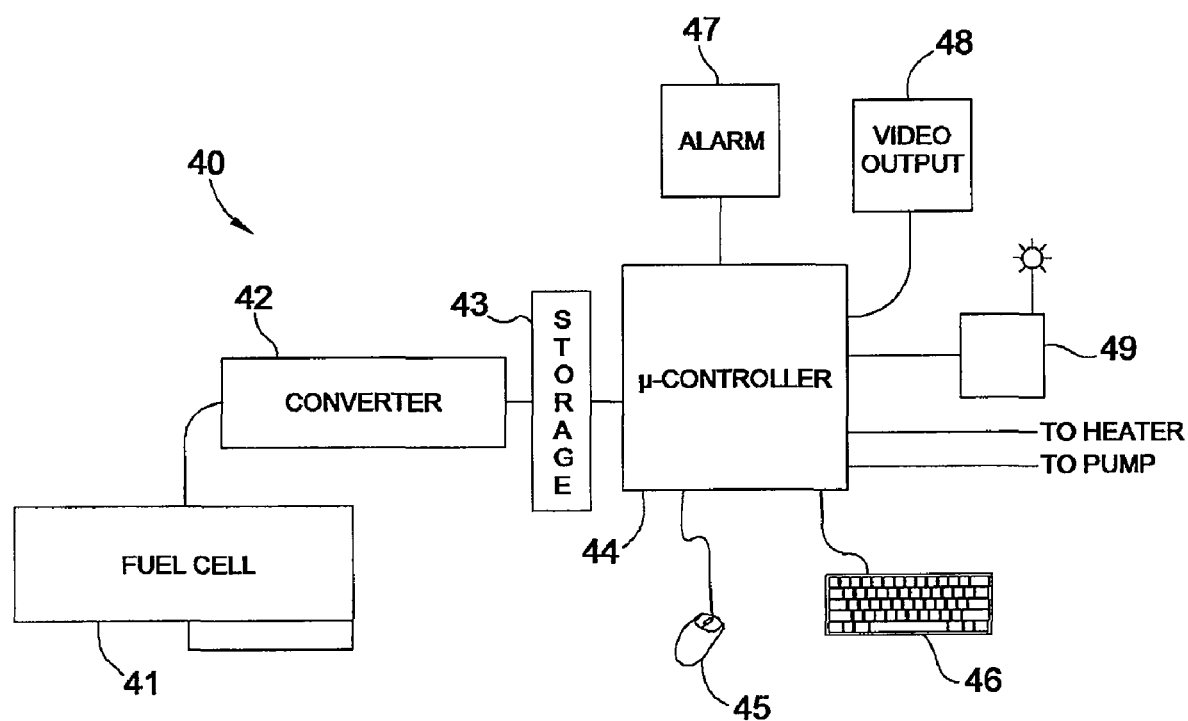
FIG. 4 depicts a wearable dialysis system powered by a fuel cell.
Figure 7:
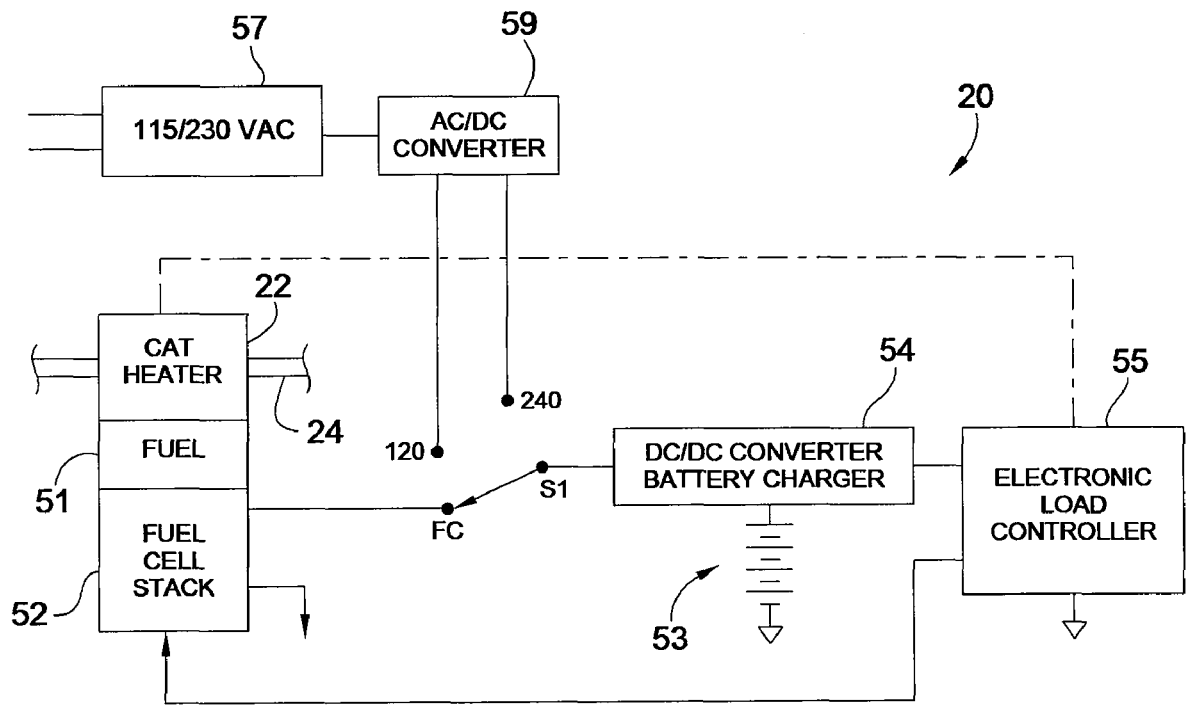

Another embodiment of a dialysis machine control system 40, as shown in FIG. 4, is more suited to a portable apparatus, e.g., one worn by a patient, as shown in FIG. 7. In this embodiment, power is provided by fuel cell 41 with a replaceable fuel cartridge, converted by conversion circuit 42, and stored in an optional energy storage device 43, such as a battery or a capacitor. The microcontroller 44 controls the device using inputs from a mouse 45 and keypad 46. The control system also has outputs including alarm 47 and a video output 48, which may be a very small device, for example, one that displays the time remaining in a dialysis treatment. In this embodiment, the control system 40 also includes a radio 49, for wireless communication to another device, such as a hospital or clinic intranet. In some embodiments, the dialysis machine control system 40 may also include switches or other electromechanical inputs for signaling the microcontroller 44 and controlling the operation of the system. The converter 42 may also accept power from other power sources, such as a vehicle electrical system (12 VDC or 24 VDC) or other usable voltage. The portable dialysis machine may thus be mounted on and receive power from an electric cart, an electric wheelchair, an automobile, a truck, or other movable vehicle.

The radio or wireless receiver/transmitter 49 is small and compact, and is easily placed on a portable dialysis system. One radio that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The control portion 40, as noted, is intended for close proximity, within range of the ZigBee module, of about 10-20 feet, of an wireless antenna or receiver. Thus, the portable machine is conveniently small and unobtrusive for the patient, but fully capable of communication and control with a hospital information system or other network.

Figure 5:
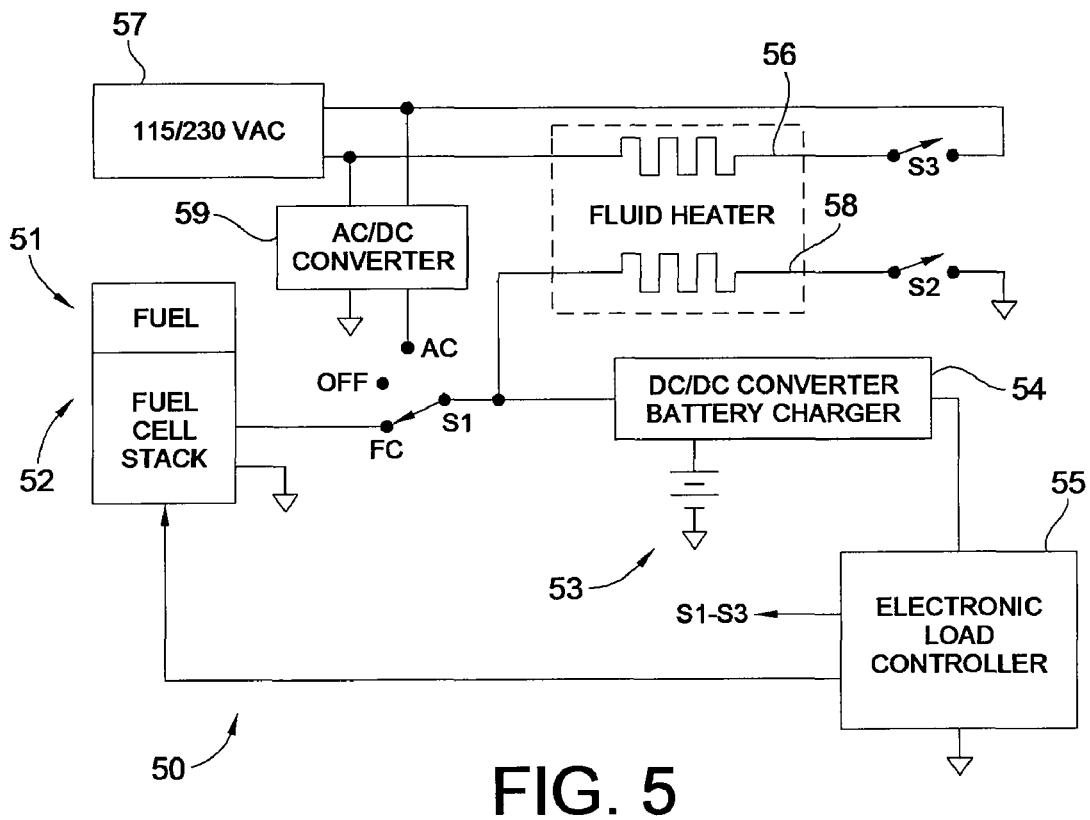
FIGS. 5-7 depict power supplies for medical fluid delivery systems using fuel cells.
Figure 6:
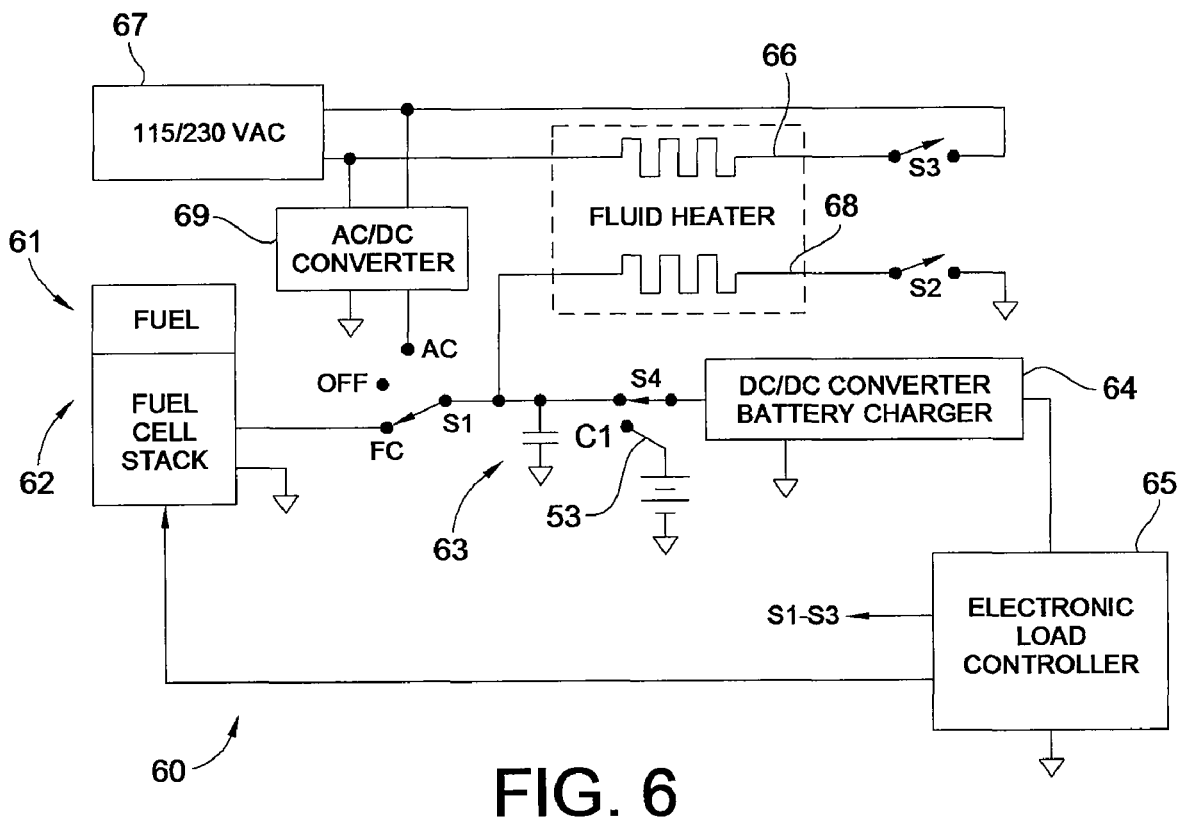

FIGS. 5-6 depict fuel cells and power supplies for using the electricity from fuel cells. FIG. 5 depicts a power circuit 50 for a dialysis machine, the power circuit including a fuel supply or fuel cartridge 51, a fuel cell stack 52, and a battery 53 for supplying enough electricity to start the system in the case when AC power 57 is not available to start the fuel cell operation. The battery may also supplement power from the fuel cell when the power requirements exceed the available power from the fuel cell or the battery may be charged by the fuel cell when excess power is available from the fuel cell that is not being used by the remainder of the electrical load. In the case when the fuel cell is not operational, AC power may maintain the charge on the battery. The electrical potential generated from a single fuel cell will be typically about 0.7 to about 1 VDC. Thus, in this example the fuel cells will be ganged or stacked in series to achieve a useful voltage, such as at least 5 VDC. In the case of a heater with a needed power output of about 450 W, an output voltage of about 30 V may be needed to reduce the required heater current to reasonable levels. Once a useful voltage is achieved, by stacking or other technique, DC power may be used for a microcontroller or other control devices.

The system depicted in FIG. 5 minimizes power conversion losses by supplying power directly to a heating element from the power source without using an AC to DC converter 59 in the case of an AC power source or a DC to DC converter in an embodiment in which the fuel cell is the power source. Note that the AC to DC converter 59 that is used to supply power to the remainder of the electric/electronic load, including the controller, may utilize a power factor correction circuit to minimize current harmonics on the AC power line, as required by some electromagnetic compatibility standards. As discussed above, DC power, or even AC power, may be available for a portable dialysis machine from the battery or from a generator or alternator of a moving vehicle. In one embodiment, the DC/DC converter 54 may accept such DC power directly for powering the portable dialysis machine.

If standard 115 VAC power is available, a typical heating element has a resistance of 30 Ohms, providing the needed 450 W to the heating element. When less power is required, switch S3 is opened, reducing the instantaneous power to zero. In general, a pulse width modulation (PWM) signal is applied to control the average power delivered to the heating element. The PWM is controlled by a Proportional-Integral-Differential (PID) control loop to maintain the desired temperature on the heater pan. The needed power may be supplied to the heating element by a 115 VAC power source connected to a 30-ohm heating element or by a 230 VAC power source connected to a 120-ohm heating element. The temperature control of the heating element is controlled as described above using a PID controller. Although not shown, a heating pan may include 2 resistive heating elements each with a resistance of 60 ohms. For 115 VAC power, a series of switches places the 60 ohm resistive heating elements in parallel, effectively creating the desired 30 Ohm heating element. For 230 VAC power, another series of switches places the 60 Ohm heating elements in series, creating the desired 120 Ohm resistive heating element. The implementation of this network of switches is familiar to those skilled in electrical arts.

In one embodiment, the fuel cell supplies power to the heater and the heating element has a resistance of 2 ohms. This requires a fuel cell voltage output of about 30 VDC to generate the needed 450 Watts. This may require a power source with 40 fuel cells in series. As described above, when less than the maximum power is required, S2 is opened using a PID controller providing the desired amount of average power to the heating element.

In the event that AC power 57 is available when the dialysis machine is required to be turned on, the user or control system would move switch S1 to the AC position allowing a DC/DC converter/battery charger 54 to power the control system 55 to an operational state from a standby state. The dialysis machine would start its normal operation, and battery charging would start if required. If required, the AC-powered heating element 56 would be activated by closing switch S3 and modulated to maintain the proper energy flow into the heater pan. In the event of AC power loss, the battery supplies power to controller 55 while the heater 58, controlled by closing switch S2, would be turned off to conserve energy from the battery. The controller or control system 55 would enable fuel to reach the fuel cell stack 52 and S1 would be switched to the FC position to connect electric power from the fuel cell stack 52 to the converter/battery charger 54. As power becomes available from the fuel cell, the battery 53 supplies less power until enough power is available from the fuel cell to supply power to the heating element, by modulating switch S2, and recharge the battery. When AC power is restored the process is reversed so that the fuel cell can be turned off. When no AC power is available, the battery 53 supplies the power to turn the fuel cell on without first going through the switch to AC power state.

A second embodiment of a power circuit 60 is depicted in FIG. 6. In this embodiment, a fuel supply 61 is connected to a fuel cell stack 62. An energy storage device 63, a capacitor or super-capacitor, is used to temporarily store electricity generated by fuel cell 62. The capacitor is not intended as a filter, but as a rather large energy storage device, i.e., a capacitor capable of storing up to 20 Farads at 30 VDC. The capacitor depicted in FIG. 6 is actually a combination of many low voltage/high capacitance capacitors placed in series, and also in parallel, to create the required capacitance and voltage capacities. The basic capacitors, known as electric double layer capacitors, are available from a variety of manufacturers, such as Cornell Dubilier Electronics, New Bedford, Mass., U.S.A.

Most of the remainder of the circuit components of FIG. 6 are similar to those of FIG. 5, including switches S1, S2, S3 and a new switch S4, for connecting a small battery 53 to a DC/DC converter 64 and the controller 65. These include an AC main power 67, AC/DC converter 69, heaters 66, 68, and a DC/DC converter 64. It is not expected that a super-capacitor with a full charge would provide sufficient energy to allow the instrument to power up in the case of no AC power available after a long period of storage (several days to months). Therefore, as in FIG. 6, a battery 53 would be needed in addition to the capacitor shown in FIG. 6 to allow use without AC power available at the time of startup. This small capacity battery would supply enough control energy to open the fuel valve leading to the fuel cell stack 62 to allow the fuel cell stack to generate electricity. As also noted above, DC/DC converter 64 is able to accept DC power from a moving vehicle battery or generator system to power the portable dialysis system.

Another embodiment of a fuel cell-powered dialysis system 20 is shown in FIG. 7, using an in-line heater. In-line heating of dialysis fluid is more fully explained in U.S. Pat. No. 7,153,285, which is hereby incorporated by reference in its entirety, and which patent is assigned to the assignee of the present patent. In this embodiment, fuel cell 52 is powered by fuel 51, which also fuels a catalytic in-line heater 22. Dialysis fluid flows through input tubing 24 to the patient and is heated as it passes through the catalytic heater 22. Using this technique, heat energy is used directly, with no need to first convert the heat energy into electricity. This technique thus avoids the need for the high voltages and high currents required by electrical heating of large quantities of dialysis fluid, and the technique and equipment remain useful in remote areas. Catalytic heaters, as described in U.S. Pat. Nos. 5,326,252, and 5,842,851, which are hereby incorporated by reference in their entirety, are useful for supplying heat energy directly from fuel, such as methanol or ethanol. Appropriate control is provided by the catalytic heater controls, and by the system controller 55. The remainder of system 20 includes an AC power connection 57, an AC/DC converter 59, a storage battery 53 and a DC/DC converter 54, which operate substantially as described for system 50 in FIG. 5. Switch S1 is operative to connect the DC/DC converter to electricity from the fuel cell stack 52, 120 VAC, or 240 VAC.

Catalytic heaters are useful in a variety of applications, such as small hand and feet warmers that use alcohol as fuel, as in U.S. Pat. No. 4,068,651, which is hereby incorporated by reference in its entirety. An in-line catalytic heater useful for warming the dialysate fluid may use methanol or other fuel, as mentioned in U.S. Pat. No. 4,659,634, which is hereby incorporated by reference in its entirety. A catalytic heater which relies on its fuel and ambient air tends to be self-limiting, as described in U.S. Pat. No. 5,037,293, and thus, with proper control, very safe. U.S. Pat. No. 5,037,293 is also incorporated by reference in its entirety. In such systems, the catalytic heater is connected to the system controller and is monitored by at least one temperature indicator, such as a thermocouple or thermistor, which monitors and reports the temperature of the dialysis fluid into and out of the catalytic heater. Catalytic heaters are available from a number of manufacturers, including Coleman Co., Wichita, Kans.; Century Tool & Mfg. Antioch, Ill.; Master and Reddy heaters are available from the DESA Company, Bowling Green, Ky.

Figure 8:
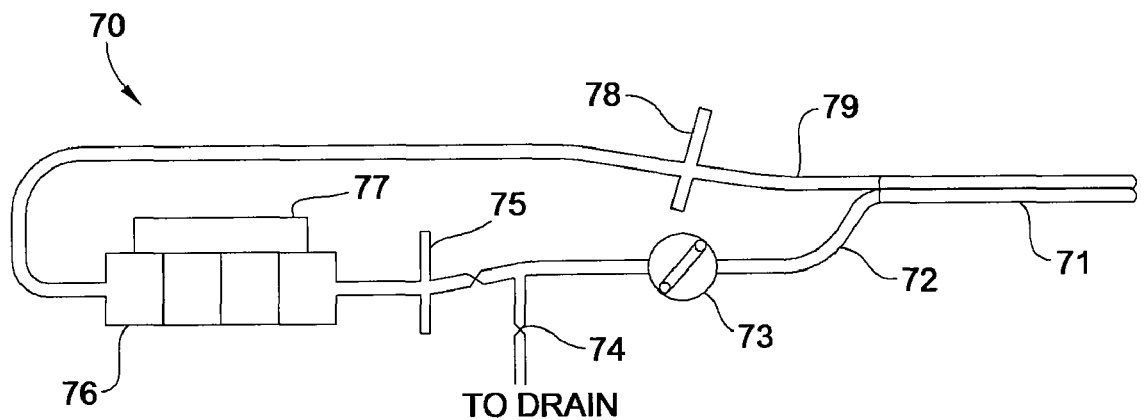
FIG. 8 depicts a portable, wearable dialysis system with a fuel cell power source.

A portable, wearable dialysis device 70 is depicted in FIG. 8. The patient access 71 may be a dual-lumen device as shown. Alternatively, the portable device could utilize a single-lumen access device and provide a container for temporary storage of the spent dialysate while it is being pumped from the peritoneum of the patient for re-cycling back into the peritoneum. The dialysis device 70 also includes tubing 72, such as flexible tubing and a pump 73, such as a peristaltic pump or other positive-displacement pump, for easily controlling the flow of fluid to and from the patient.

The dialysis device includes a first drain valve 74, leading to a drain bag (not shown) which would likely not be carried by the mobile patient, but would be available for a draining situation. A particulate filter 75 would help to eliminate particulates and debris from the fluid circuit, before the dialysis fluid to be treated encounters disposable cartridge 76. Disposable cartridge 76 in this embodiment includes several layers for removal of different toxins from used dialysate fluid. In this embodiment there is a carbon or charcoal layer for removing creatinine and other organic toxins. There is a layer with urease and an absorbent, such as zirconium oxide, for removing urea. There is also a layer with a sorbent or an ion exchange resin for removing phosphate and sulfate, such as zirconium phosphate. The fourth layer is a second layer of zirconium oxide and urease for removing urea. In other embodiments, the extra or fourth layer may be different. Because the cartridge is relatively large, the fuel cell 77 and its associated fuel supply are mounted to the cartridge. In one embodiment, the fuel cell and its fuel supply may be carried in a backpack rather than being worn on a belt. In another embodiment, the fuel cell 77 may be mounted on the pump 73, which is bulky compared with most of the remaining parts. An antimicrobial filter 78 may also be used, as shown, as a final polish on the renewed and refreshed dialysate fluid on its way through tubing 79 to the other lumen of the patient access device 71. In one embodiment, the fuel cell and its associated power storage and conversion system are configured to accept standard AC wall-outlet power or DC battery power, as discussed above, for situations in which it is desired to use the portable dialysis machine in a stationary mode. This would occur, for example, at home or when riding for a period of time on a moving vehicle.

The portable, wearable dialysis system described above is suitable for peritoneal dialysis in which the dialysis fluid is continuously or periodically cycled through the filters and sorbent pack to remove toxins and impurities from the dialysis fluid. A portable hemodialysis machine is also envisioned. Instead of a double lumen catheter, there is an access device that provides for flow of blood to and from the person. There are two pumps, one for the blood and another for pumping dialysis fluid to and from a dialyzer that is also mounted on a belt or backpack for the patient. There is also at least one container for the dialysate fluid that is continuously pumped to and from the dialyzer for removing ultrafiltrate separated from the blood. The dialysis fluid is pumped through the sorbent pack in a manner similar to that for peritoneal dialysis, to remove toxins by adsorbing onto the sorbents in the pack.

Dialysis machines consume reasonable amounts of energy. In peritoneal dialysis, most of the energy is used in heating a large quantity of dialysate fluid. One estimate is the dialysis machine itself, in a quiescent state, simply running a microprocessor, small lights, etc., requires about 30 W of constant power, i.e., about 30 W-h per hour, including pumping. In addition, it requires about 305 W-h of energy for heating the dialysate from about 27 C (room temperature) to about 37 C (body temperature). For a nine-hour therapy, this totals about 9×30 or 270 W-h+305 W-h for a total of about 575 W-h over a 9-hour period. Further testing was conducted using room temperature of 10 C (50° F.), a 9-hour therapy, and an insulator on top of a bag of dialysate, for conserving heat in the dialysate bag. The dialysate container or bag is normally placed on a heater pan with its top surface exposed to room temperature air.

In this testing, it required about 730 W-h to heat the dialysate, in addition to the constant 270 W-h, for a total of about 1000 W-h. Additional tests at 10 C without a blanket required about 1120 W-h for heating, along with the constant 270 W-h, for a total of 270+1120=about 1390 W-h. Thus, power requirements may range as high as about 1390 W-h in a very cool home environment, while energy consumption of about 600 W-h would be considered more normal for peritoneal dialysis. Hemodialysis typically takes place over a 3-4 hour period, and thus would not require as long a period time as peritoneal dialysis. The dialysate or the blood is warmed to avoid temperature shock to the patient and there is significantly more pumping involved than with peritoneal dialysis. On balance, hemodialysis is expected to have higher total energy requirements than those of peritoneal dialysis because the water and concentrate, or pre-mixed dialysate, is also warmed. Under these circumstances in-line heating clearly has advantages, especially if the heat for warming is supplied separately, as described above in FIG. 7.

Figure 9:
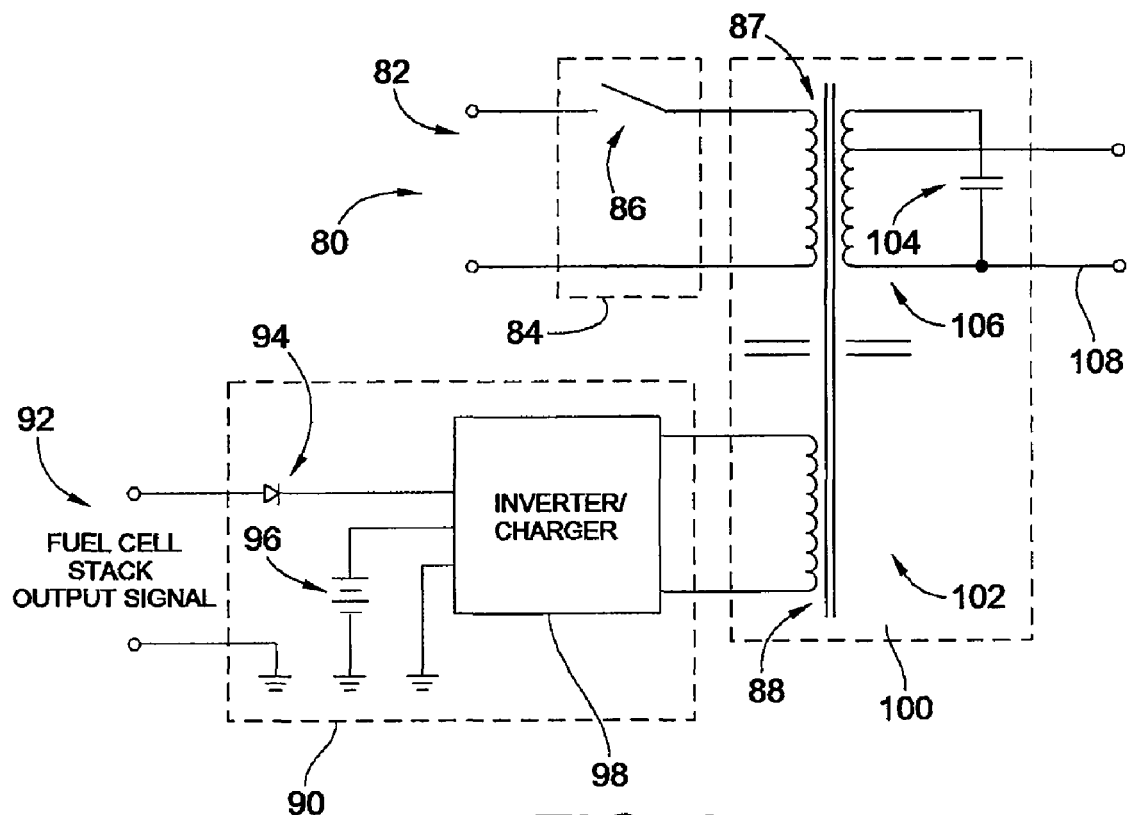
FIGS. 9-10 depict more sophisticated power and control systems using fuel cell power sources.

The above embodiments depict stand-alone power supplies for dialysis or fluid-handling machines. In other embodiments, the fuel cells described herein may be used as back-up power supplies for local household, vehicle, or utility power. FIG. 9 depicts an embodiment 80 of an AC power circuit that may be used as an uninterruptible power circuit, combining first input terminals 82 of a utility input circuit 84, for connection to a source of utility power, and a switch 86 that allows the output circuit 100 to be disconnected from the terminals 82. Fuel cell input circuit 90 includes second input terminals 92, a diode 94, battery system 96, and an inverter/charger circuit 98. The second input terminals 92 are connected to the fuel cell such that the DC fuel cell output voltage is present across terminals 92. A DC power input from a vehicle may connect in parallel with battery 96.

When the AC power generation circuit 80 generates the AC power output from the utility power, the inverter charger circuit 98 charges the battery 96. Thus, should the utility power fail, the inverter/charger circuit 98 can generate backup or secondary AC power using energy stored in the battery 96 until the fuel cell begins generating electricity. The battery would also supply power necessary to start the fuel cell producing energy, such as power for connecting the fuel source and other necessary valves or pumps. The diode 94 prevents current that charges the battery 96 from flowing back into the fuel cell or fuel cell stack.

Output circuit 100 includes a transformer 102 having first primary windings 87, second primary windings 88, and secondary windings 106. Output circuit 100 also includes a conventional capacitor 104 connected across the secondary windings 106. Output terminals 108 are connected across a portion of the secondary windings 106 for connection to the AC power connector on the dialysis machine. The first primary windings 87 are connected through the switch 86 to the first input terminals 82. Second primary windings 88 are connected to the inverter/charger circuit 98. With these connections, the output AC power signal is present across the output terminals 108.

The transformer 102 and capacitor 104 regulate AC power output, as is well-known in the art. If the fuel cell is supplying power through transformer 102 to output terminals 108 with switch 86 open (as in the case of an AC power failure), and AC power is restored, the inverter/charger can synchronize with the AC mains connected at terminals 82 and stop supplying power to the transformer at the same time switch 86 is closed, to allow the AC mains to supply power to terminals 108. This system may be equipped with a status monitoring and control system to detect such. This embodiment uses battery 96 to store power for temporary outages. A DC power output for the control system of the inverter/charger and fuel cell valves and pumps may be taken from the battery.

Figure 10:
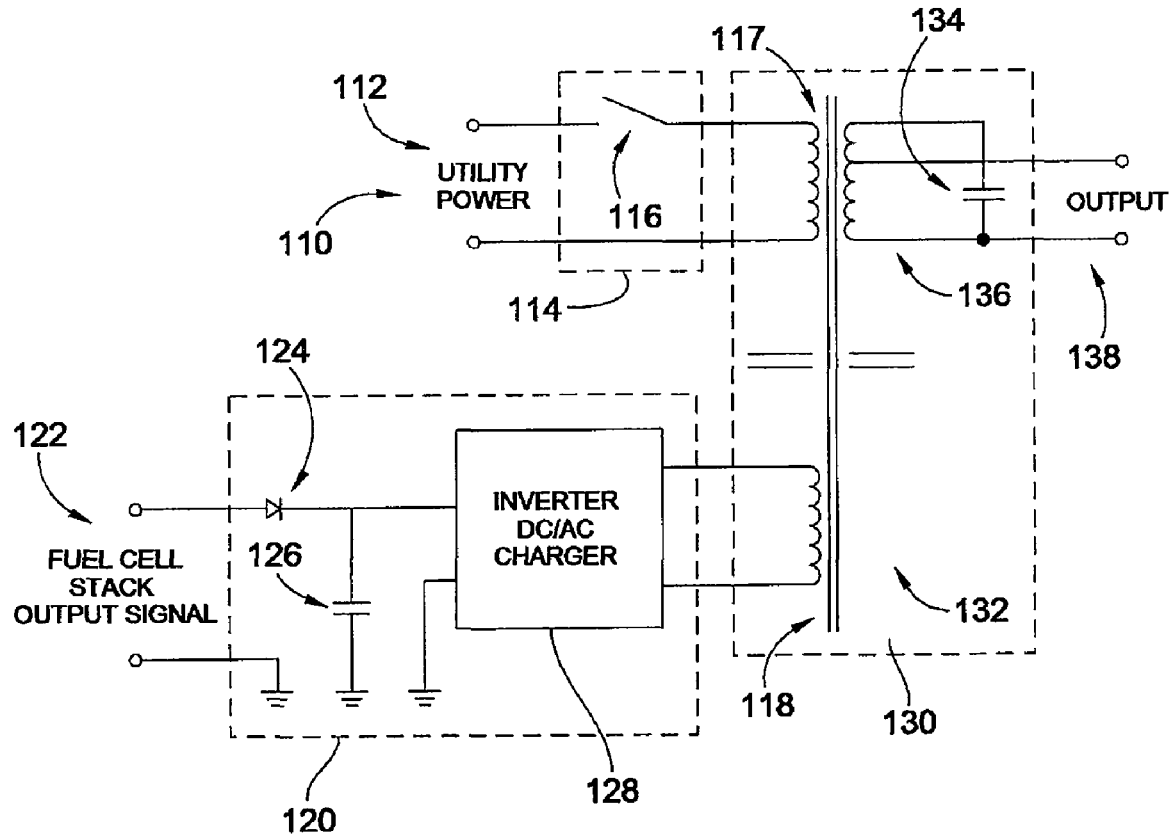

Another embodiment, in FIG. 10, uses a large capacitor for energy storage. The utility input circuit 114 of the generation circuit 110 includes first input terminals 112 connected to a source of utility power and a switch 116 that allows the output circuit 130 to be disconnected from utility input terminals 112. The fuel cell input circuit 120 includes second input terminals 122, a diode 124, storage capacitor 126, and an inverter/charger circuit 128. Second input terminals 122 are connected to the fuel cell stack so the DC fuel cell output voltage is present across terminals 122.

When the AC power generation circuit 110 generates the AC output power from the utility power, the inverter charger circuit 128 charges the storage capacitor 126. Thus, should the utility power fail, the inverter/charger circuit 128 can generate secondary or backup AC power using the energy stored in super-capacitor 126 until the fuel cell begins generating electricity. The super-capacitor would also supply power necessary to start the fuel cell to produce energy, such as power for connecting the fuel source and other necessary valves or pumps. Diode 124 prevents current from flowing back into the fuel cell.

Output circuit 130 includes a transformer 132 having first primary windings 117, second primary windings 118, and secondary windings 136. The output circuit 130 further includes a conventional capacitor 134 connected across the secondary windings 136. The circuit output terminals 138 are connected across a portion of the secondary windings 136 and are intended for connection to the AC power connector on the dialysis machine. The first primary windings 117 are connected through the switch 116 to the first input terminals 112. The second primary windings 118 are connected to the inverter/charger circuit 128. So connected, the output AC power output is present across the output terminals 138. The transformer 132 and capacitor 134 regulate the AC power output.

If the fuel cell is the primary energy source and the fuel cell output is disrupted, sufficient energy is stored by the large capacitor 126 to maintain the AC power output until the switch 116 can be closed to allow the AC utility power to reach the output circuit 130. The system may be equipped with a status monitoring and control system to detect such changes, or it may be operated manually.

Figure 11:
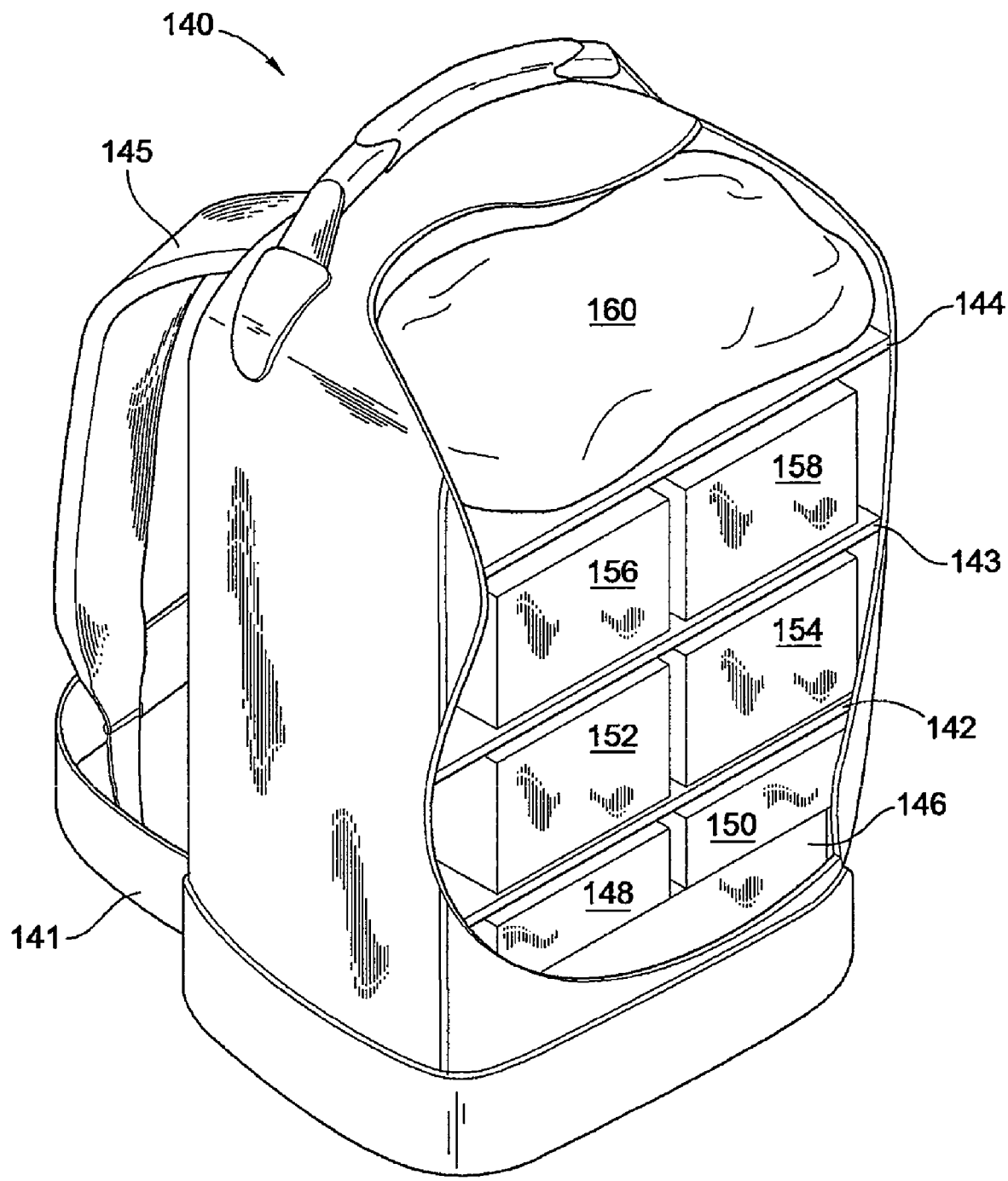
FIG. 11 depicts another embodiment of a portable powered dialysis machine.

There are many other embodiments of a portable power dialysis system. For instance, the components may be placed into a pack that is easily transported, e.g., on a wheeled suitcase or luggage tote, a back pack, a cart, or even as a pack for a person using a wheelchair. One example of a back pack portable power dialysis system 140 is illustrated in FIG. 11. The system is designed as a canvas or plastic back pack, with the appearance of an ordinary back pack, including a belt 141 and shoulder straps 145. In this cut-away view, the system has several shelves or tiers 142, 143, 144, for convenience in loading, unloading, and replacing various components of the system.

A battery 146, which may be bulky, is placed on the bottom of the bag, and in this embodiment, supports a fuel cannister 148 for the fuel cell 150. The fuel should be placed in the pack so that it can be readily removed and replaced with fresh fuel. The disposable or cassette portion 152 and the control portion and electronics 154 are placed above the bottom tier. The next level includes a replaceable filter cartridge 156 and a pump 158, which may be used instead of or in addition to the pump or pumps in the disposable 152. A container 160 of dialysate fluid is placed on the top tier. This particular placement of the components is not the only possible arrangement, and many other suitable arrangements are also possible. The system also includes the necessary tubing and access device for the patient. Of course, it would be convenient for the patient if the replaceable or usable components are readily accessible once the pack is opened by moving a flap or a zipper. These include tubing for an access port for the patient, the fuel for the fuel cell, the disposable, the filter cartridge, and the bag of dialysis fluid.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A portable, wearable dialysis machine for a patient, comprising:
   a fuel cell, an alternating current ("AC") power source, and a battery for powering the portable, wearable dialysis machine;
   a pump powered by the fuel cell, the AC power source, or the battery for pumping dialysis fluid in a fluid circuit;
   a particulate filter placed in the fluid circuit;
   a replaceable cartridge in the fluid circuit for absorbing waste products; and
   a controller configured so that
   (i) if the AC power source is available, the AC power source charges the battery and powers the portable, wearable dialysis machine, including the pump; and
   (ii) if the AC power source is not available
      (a) if the fuel cell is in an operational state, the fuel cell charges the battery and powers the portable, wearable dialysis machine, including the pump; and
      (b) if the fuel cell is not in an operational state, the battery powers the fuel cell to an operational state and powers the portable, wearable dialysis machine, including the pump, until the fuel cell is in an operational state.

2. The portable, wearable dialysis machine of claim 1, further comprising an antibacterial filter in the fluid circuit and upstream of an access device connected to the patient.

3. The portable, wearable dialysis machine of claim 1, wherein the patient connects to the fluid circuit with a single lumen access device or a double-lumen access device.

4. The portable, wearable dialysis machine of claim 1, wherein the fuel cell is a direct methanol or ethanol fuel cell.

5. The portable, wearable dialysis machine of claim 1, wherein the dialysis machine is a hemodialysis machine, and further comprising a container for the dialysis fluid, a dialyzer, a second pump powered by the fuel cell, and tubing connecting the dialysis fluid container to the fluid circuit and the dialyzer, and blood line tubing connecting the patient to the second pump and the dialyzer and returning to the patient.

6. The portable, wearable dialysis machine of claim 1, wherein the dialysis machine is a peritoneal dialysis machine.

7. The portable, wearable dialysis machine of claim 1, further comprising a catalytic heater for warming the dialysis fluid for the patient.

8. The portable, wearable dialysis machine of claim 7, wherein the catalytic heater is an in-line catalytic heater, the in-line catalytic heater in operable communication with the controller.

9. The portable, wearable dialysis machine of claim 1, further including a capacitor capable of storing electricity.

10. The portable, wearable dialysis machine of claim 1, further including a heating element for heating the dialysis fluid, wherein if the AC power source powers the portable, wearable dialysis machine, the AC power source powers the heating element without using an AC to DC converter, and if the fuel cell powers the heating element, the fuel cell powers the heating element without using a DC to DC converter.

11. The portable, wearable dialysis machine of claim 10, which is configured such that if the heating element receives more power than necessary from the fuel cell, a switch inside the portable, wearable dialysis machine is opened to reduce the power to the heating element.

* * * * *